United States Patent [19]

Astoin

[11] 4,337,252
[45] Jun. 29, 1982

[54] 1-PHENYL-4-MORPHOLINO-1-BUTEN-3-01 DERIVATIVES, COMPOSITIONS AND USE

[75] Inventor: Jacques N. Astoin, Paris, France

[73] Assignee: Univablot, Paris, France

[21] Appl. No.: 224,739

[22] Filed: Jan. 13, 1981

[30] Foreign Application Priority Data

Jan. 16, 1980 [FR] France ............................. 80 00890

[51] Int. Cl.³ .................... A61K 31/535; C07D 295/08
[52] U.S. Cl. ............................ 424/248.57; 424/248.58; 542/400
[58] Field of Search .................. 542/400; 424/248.57, 424/248.58

[56] References Cited
U.S. PATENT DOCUMENTS
4,209,517  6/1980  Riveron .......................... 424/248.57

FOREIGN PATENT DOCUMENTS 2381765  2/1977  France .

Primary Examiner—Henry R. Jiles
Assistant Examiner—R. W. Ramsuer
Attorney, Agent, or Firm—Wegner & Bretschneider

[57] ABSTRACT

The compounds have the formula:

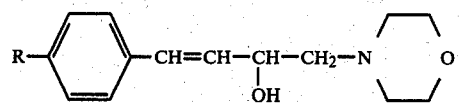

in which R is OH, $OCH_3$, $OCH_2CH=CH_2$ or $OCH_2-C\equiv CH$, or a halogen atom, as well as their addition salts. The compounds have anti-depressant properties.

5 Claims, No Drawings

1-PHENYL-4-MORPHOLINO-1-BUTEN-3-OL DERIVATIVES, COMPOSITIONS AND USE

The present invention relates to new compounds derived from 1-phenyl-4-morpholino-1-buten-3-ol, their preparation, and their application in therapeutics.

α-Ethylenically unsaturated alcohols are known that can be used in therapeutics and have a structure similar to that of the compounds of the invention, in particular the compounds according to French Patent of Addition No. 77.05213 (publication No. 2 381765) corresponding to U.S. Pat. No. 4,029,517. It has unexpectedly been found that some compounds relatively similar from the structural point of view have more specific pharmacological properties, and in particular a longer action. It appears that this activity is due to the para position of the substituent on the phenyl nucleus since the isomers of these compounds as well as the compounds bearing several substituents on the phenyl nucleus are found to be inactive. In fact, the applicants have prepared and subjected to pharmacological tests, compounds of the formula

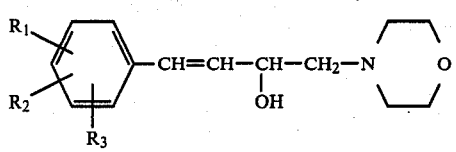

in which $R_1$, $R_2$ and $R_3$ each denote independently H, $CH_3$, OH, $-OCH_3$, $-OC_2H_5$, $-OiC_3H_7$, allyloxy, propargyloxy or halogen, as well as their addition salts, in particular their hydrochlorides, and most of these compounds were only slightly active or were inactive.

The compounds of the invention have the formula:

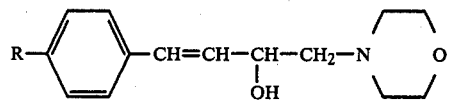

in which R denotes a OH, $OCH_3$, $OCH_2CH=CH_2$ or $OCH_2C\equiv CH$ radical or a halogen atom, as well as their pharmaceutically acceptable addition salts.

The pharmaceutically acceptable addition salts are those obtained with the acids normally used in pharmacy, especially those that render the compounds soluble. Since the compounds (I) are slightly basic, strong acids, for example HCl, are preferably used.

The compounds of the invention may be prepared by condensing a benzaldehyde of the formula III and morpholinoacetone (IV), and then reducing the ketone (II) thus obtained, according to the following reaction scheme:

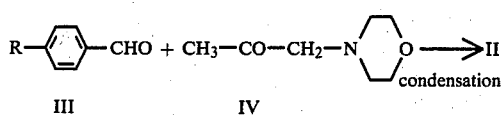

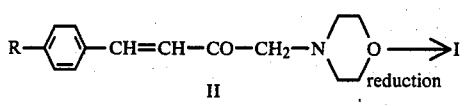

This condensation (crotonisation) may be effected in a conventional manner, for example in an aqueous and/or alcoholic medium, at ambient temperature, and from equimolecular amounts of aldehyde (III) and ketone (IV). The reduction of the ketone (II) to alcohol (I) is carried out in a conventional manner, for example by means of sodium or potassium borohydride in an alcoholic medium.

The compounds of the invention may also be prepared by reacting the organo-magnesium reagent of an acetylenically unsaturated phenyl derivative (V) with morpholinoacetonitrile (VI) according to the reaction scheme:

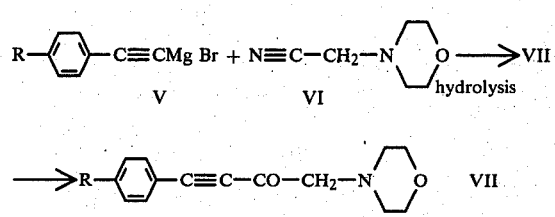

The α-acetylenically unsaturated ketone (VII) may be reduced directly to the α-ethylenically unsaturated alcohol (I), for example by means of $LiAlH_4$. The organomagnesium reagent (V) is prepared in a conventional manner from ethylmagnesium bromide (obtained in situ from ethyl bromide and magnesium) and a phenyl-acetylene bearing the substituent R.

In the preceding formulae (II, III, V and VII), the symbol R has the same meaning as in formula I.

The following example illustrates the preparation of the compounds of the invention according to the first method described above.

EXAMPLE 1-(p-methoxyphenyl)-4-morpholino-1-buten-3-ol and its hydrochloride (Code No. 1711)

(a) *Condensation* 13.6 g (0.1 mole) of p-methoxybenzaldehyde is dissolved in 14.3 g (0.1 mole) of morpholinoacetone and this solution is added dropwise to 100 cm³ of a solution of 1 N sodium hydroxide cooled in an ice-containing water bath. The temperature is allowed to return to ambient temperature while stirring for 5 hours. The precipitate obtained is filtered and rinsed several times with water. 18.8 g of 1-(p-methoxyphenyl)-4-morpholino-1-buten-3-one is obtained.

m.p.=78° C.

yield=72%.

Reduction 26.1 g (0.1 mole) of 1-(p-methoxyphenyl)-4-morpholino-1-buten-3-one is dissolved in 300 ml of methanol and an aqueous solution of $KBH_4$ is added dropwise in excess. The reaction mixture is left to stand overnight and is then poured onto water, filtered, and the product obtained is washed. The product is recrystallised in cyclohexane.

m.p.=88° C.

yield=80%.

(c) Hydrochloride 1-(p-methoxyphenyl)-4-morpholino-1-buten-3-ol is added to an excess of ether hydrochloride (HCl dissolved in diethyl ether). The hydrochloride thus obtained is recrystallised in ethanol.

m.p.=210° C.

The Table I following gives the compounds of the formula I as well as other compounds of the structure of formula I', prepared according to the previous example, their melting points (F) and the recrystallisation solvent.

$$R-\text{C}_6\text{H}_4-CH=CH-CH(OH)-CH_2-N\diagup\!\!\diagdown O \quad \text{I}$$

| Example No. | Code No. | R | F base solvent | F hydro-chloride solvent |
|---|---|---|---|---|
| 1 | 1711 | $CH_3O$ | 88° cyclohexane | 210° ethanol |
| 2 | 1837 | Cl | 82° cyclohexane | 208° ethanol |
| 3 | 1844 | F | 74° cyclohexane | 158° ethanol |
| 4 | 1836 | OH | 132° ethanol 50% | 215° ethanol |
| 5 | 1841 | $OCH_2C\equiv CH$ | 110° ethanol | 174° ethanol |
| 6 | 1889 | $OCH_2CH=CH_2$ | 62° cyclohexane | 192° ethanol |

$$R_1,R_2,R_3-\text{C}_6\text{H}_2-CH=CH-CH(OH)-CH_2-N\diagup\!\!\diagdown O \quad \text{I'}$$

| Example No. | Code No. | $R_1, R_2, R_3$ (position on phenyl) | F base solvent | F hydro-chloride solvent |
|---|---|---|---|---|
| 7 | 1712 | $(CH_3O)_2$ (2,4) | 80° ethanol-water 50/50 | 180° ethanol |
| 8 | 1492 | $(CH_3O)_2$ (2,5) | 56° petroleum ether | 166° ethanol |
| 9 | 1843 | $(CH_3O)_2$ (3,4) | 72° cyclohexane | 138° ethanol |
| 10 | 1713 | $(CH_3O)_3$ (2,3,4) | 75° petroleum ether | 166° ethanol |
| 11 | 1714 | $(CH_3O)_3$ (2,4,6) | 120° ethanol | 190° ethanol |
| 12 | 1842 | $(CH_3O)$ (2) | 65° petroleum ether | 158° ethyl acetate |
| 13 | 1838 | $(i\text{-}C_3H_7O)$ (4) | 70° cyclohexane | 210° ethanol |
| 14 | 1872 | H | oily liquid | 214° ethanol |
| 15 | 1817 | (OH) (4) ($CH_3O$) (3) | 96° cyclohexane | 168° ethanol |
| 16 | 1819 | (OH) (3) ($CH_3O$) (4) | 118° ethanol 50% | 172° ethanol |
| 17 | 1873 | ($CH_3$) (4) | 88° cyclohexane | 236° ethanol |
| 18 | 1869 | ($CH_3O$) (2) | 74° cyclohexane | 142° ethanol |

The compounds of the invention were subjected to pharmacological tests.

A. Toxicity

The $LD_{50}$ of the products was measured in mice by the intraperitoneal route according to the "log-probits" method of Miller and Tainter (Proc. Soc. Exptl. Biol. Med. 1944; 57, 261-264).

B. Activity on the central nervous system

This was investigated by observing the behaviour of the animal, by studying the change in hexobarbital-induced narcosis, and by studying the anti-convulsant capability and reserpine antagonism.

1. Modification of hexobarbital-induced narcosis

Mice weighing about 20 g each receive the product being studied intraperitoneally at a dosage of 1/10 of their $LD_{50}$. Half an hour later sodium hexobarbital is injected by the same route at a dosage of 70 mg/kg.

The animals are placed on a heated plate maintained at a constant temperature of 27° C. It is considered that sleep is induced when a mouse, placed on its back, is incapable of righting itself.

The narcosis potentialisation is evaluated by the percentage increase in the sleeping time induced by hexobarbital (T).

2. Anti-convulsant action (Boissier—Actualités Pharmacologiques, 12th series, page 1)

(a) Pentetrazole-induced attack

The convulsive attack is produced by pentetrazole which, injected intraperitoneally into mice at a dosage of 125 mg/kg, produces 100% mortality in 5 to 7 minutes.

Mice weighing about 20 g each receive the product being investigated intraperitoneally in a dosage of 1/10 of their $LD_{50}$ 30 minutes before the pentetrazole. The time of occurrence of death with respect to that (t) of the controls, which did not receive the product, as well as the percentage protection (P) are determined.

(b) Electric shock

The application of an electric current of 30 volts for 0.5 second to the cerebral centres produces an epileptic attack.

Male rats weighing 180 to 200 g receive the solvent or product being studied intraperitoneally, at a dosage of 1/10 of their $LD_{50}$. 30 minutes later, the animals are subjected to an electric shock. It is then observed whether the attack is complete or incomplete, and the percentage protection (P) obtained by virtue of the product administered is determined.

3. Reserpine antagonism (blepharospasm) (Chen G., and Bohner B., (1961) J. Pharmacol. Exptl. Therap. 131, 179).

Reserpine administered to mice in a dosage of 5 mg/kg intraperitoneally subsequently causes the eyelids to drop more or less completely in the majority of the animals. The administration of certain products inhibits the blepharospasm produced by reserpine.

Male, Swiss strain mice are distributed into groups of 10 and each experiment comprises at least 3 groups:

a control group that receives only the solvent and reserpine a group treated with a reference product: we chose imipramine a treated group that receives the product being tested in a dosage of 1/10 of the $LD_{50}$.

The products being tested are administered intraperitoneally 30 minutes before the intraperitoneal injection of reserpine in a dosage of 5 mg/kg, so as to study their activity as a function of time.

The degree of ptosis for each eye and for each animal is observed every 30 minutes for 4 to 5 hours, according to RUBIN's scoring system (RUBIN et al., J. Pharm. Exp. Thérap. 1957, 120, 125-136). The activity of the product is determined by comparing the result obtained with the treated control group. The inhibition of blepharospasm is recorded from 0 to +++.

|   |                  |
|---|------------------|
| 0 | inhibition 0–15% |
| + | inhibition 16–25% |
| ++ | inhibition 26–45% |
| +++ | inhibition >45% |

C. Results

The results obtained in the various tests showed that no compound potentialises hexobarbital-induced narcosis, and does not protect against convulsive attacks produced by pentetrazole or electric shocks, contrary to the majority of the compounds described in the certificate of addition No. 77 05213 mentioned previously.

However, certain compounds (Examples 1 to 6 above) have an excellent antagonistic effect with respect to reserpine (blepharospasm), as can be seen from the following Table II. The other compounds are much less active (+) or are inactive.

TABLE II

| Example | Code No. | $LD_{50}$ (mg/kg) IP | Blepharospasm (mg/kg) IP |
|---|---|---|---|
| 1 | 1711 | 500 | +++ |
| 2 | 1837 | 400 | +++ |
| 3 | 1844 | 800 | ++ |
| 4 | 1836 | 650 | ++ |
| 5 | 1841 | 400 | ++ |
| 6 | 1839 | 300 | ++ |

As can be seen from the results of the pharmacological tests described above, the compounds of the invention act on the central nervous system and may be used in particular to treat depressive states.

The compounds of the invention may be formulated in association with a pharmaceutically compatible excipient for oral administration, for example in the form of tablets, pills or capsules, or for parenteral administration in the form of injectable solutions.

The daily dosage will be of the order of 50 to 250 mg orally and, where appropriate, 5 to 50 mg by injection (by perfusion) for the soluble compounds (addition salts).

| Example of capsule formulation | |
|---|---|
| Compound of Example 1 (1711) | 50 mg |
| Starch maize | 125 mg |
| Mannitol | 15 mg |
| Alginic acid | 1 mg |
| Sodium alginate | 0.1 mg |
| Talcum | 6 mg |
| Glycerol palmitostearate | 3 mg |

I claim:

1. A compound having the general formula I:

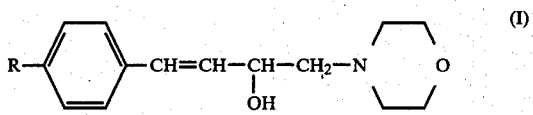

in which R is OH, OCH$_3$, OCH$_2$CH=CH$_2$ or OCH$_2$—C≡CH or a halogen atom, and the pharmaceutically-acceptable addition salts thereof.

2. The compound as claimed in claim 1, wherein in formula I R is OCH$_3$ or Cl.

3. 1-(p-Methoxyphenyl)-4-morpholino-1-buten-3-ol and its hydrochloride addition salt.

4. A pharmaceutical composition comprising, as a pharmaceutically-active ingredient, an antidepressant effective amount of a compound as claimed in any one of claims 1 to 3 together with a pharmaceutically-acceptable carrier or diluent.

5. A method for treating depressive states in a patient which comprises administering to said patient a therapeutically effective amount of a compound of claim 1.

* * * * *